(12) United States Patent
Castelein et al.

(10) Patent No.: US 10,610,262 B2
(45) Date of Patent: Apr. 7, 2020

(54) SPINAL DISTRACTION SYSTEM

(71) Applicant: UMC UTRECHT HOLDING B.V., Utrecht (NL)

(72) Inventors: Rene Marten Castelein, Almere (NL); Moyo Chikondi Kruyt, de Bilt (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 0 days.

(21) Appl. No.: 15/604,199

(22) Filed: May 24, 2017

(65) Prior Publication Data

US 2018/0338782 A1 Nov. 29, 2018

(51) Int. Cl.
*A61B 17/70* (2006.01)
*A61B 17/56* (2006.01)
*A61B 17/68* (2006.01)

(52) U.S. Cl.
CPC ........ *A61B 17/7025* (2013.01); *A61B 17/702* (2013.01); *A61B 17/705* (2013.01); *A61B 17/7028* (2013.01); *A61B 17/7049* (2013.01); *A61B 17/7074* (2013.01); *A61B 17/704* (2013.01); *A61B 2017/564* (2013.01); *A61B 2017/681* (2013.01)

(58) Field of Classification Search
CPC ........................................ A61B 17/7002–7031
See application file for complete search history.

(56) References Cited

U.S. PATENT DOCUMENTS

| 5,733,284 | A | 3/1998 | Martin | |
|---|---|---|---|---|
| 8,202,301 | B2* | 6/2012 | Prevost | A61B 17/702 606/257 |
| 8,430,916 | B1 | 4/2013 | Winslow et al. | |
| 9,408,639 | B2* | 8/2016 | Miladi | A61B 17/7014 |
| 9,770,266 | B2* | 9/2017 | Hestad | A61B 17/702 |
| 2004/0049190 | A1* | 3/2004 | Biedermann | A61B 17/7008 606/257 |
| 2005/0203509 | A1* | 9/2005 | Chinnaian | A61B 17/6491 606/54 |
| 2006/0009767 | A1* | 1/2006 | Kiester | A61B 17/7004 606/258 |
| 2006/0142758 | A1 | 6/2006 | Petit | |
| 2006/0149229 | A1 | 7/2006 | Kwak et al. | |
| 2006/0247637 | A1* | 11/2006 | Colleran | A61B 17/7007 606/257 |
| 2007/0088359 | A1* | 4/2007 | Woods | A61B 17/7026 606/86 A |
| 2008/0154307 | A1* | 6/2008 | Colleran | A61B 17/7025 606/257 |
| 2008/0195100 | A1* | 8/2008 | Capote | A61B 17/7091 606/71 |

(Continued)

FOREIGN PATENT DOCUMENTS

| CN | 105250018 A | 1/2016 |
|---|---|---|
| EP | 2047814 A1 | 4/2009 |

(Continued)

*Primary Examiner* — Jacqueline T Johanas
(74) *Attorney, Agent, or Firm* — Mannava & Kang, P.C.; Carol L. Bunner

(57) ABSTRACT

A spinal distraction system including a bearing connector fastened to a fixated rod and a sliding rod, wherein the sliding rod includes a spring and a stop ring is disclosed. A method of distracting vertebrae is also disclosed.

17 Claims, 11 Drawing Sheets

(56) References Cited

U.S. PATENT DOCUMENTS

| | | | |
|---|---|---|---|
| 2008/0262554 A1* | 10/2008 | Hayes | A61B 17/7005 606/278 |
| 2009/0204156 A1 | 8/2009 | McClintock et al. | |
| 2009/0281575 A1* | 11/2009 | Carls | A61B 17/70 606/278 |
| 2010/0106192 A1* | 4/2010 | Barry | A61B 17/7004 606/258 |
| 2011/0022095 A1* | 1/2011 | Fanger | A61B 17/7005 606/264 |
| 2011/0077687 A1* | 3/2011 | Thompson | A61B 17/7004 606/254 |
| 2011/0137353 A1* | 6/2011 | Buttermann | A61B 17/7001 606/305 |
| 2011/0152941 A1 | 6/2011 | Graf | |
| 2011/0270314 A1* | 11/2011 | Mueller | A61B 17/704 606/264 |
| 2013/0268003 A1* | 10/2013 | Hwang | A61B 17/7052 606/251 |
| 2013/0338712 A1* | 12/2013 | Massenzio | A61B 17/7014 606/252 |
| 2014/0309698 A1* | 10/2014 | McClintock | A61B 17/7002 606/278 |
| 2015/0012045 A1* | 1/2015 | Hestad | A61B 17/702 606/279 |
| 2015/0119939 A1* | 4/2015 | Frey | A61B 17/7046 606/258 |
| 2015/0164555 A1 | 6/2015 | Kalfas et al. | |
| 2015/0351805 A1* | 12/2015 | Miladi | A61B 17/7014 606/258 |
| 2016/0278814 A1* | 9/2016 | Seme | A61B 17/7001 |
| 2017/0265900 A1* | 9/2017 | Lai | A61B 17/701 |
| 2018/0028235 A1* | 2/2018 | Simpson | A61B 17/7017 |

FOREIGN PATENT DOCUMENTS

| | | |
|---|---|---|
| SU | 848009 A1 | 7/1981 |
| WO | WO-2013/172700 A1 | 11/2013 |

* cited by examiner

SPINAL DISTRACTION SYSTEM

FIELD OF THE INVENTION

The invention relates generally to a spinal distraction system including a first set of rods, a second set of rods, a fastener, a connector, and a spring. The spinal distraction system can be active and/or dynamic in nature.

BACKGROUND OF THE INVENTION

Spinal deformation during skeletal growth is a disorder with potential devastating consequences. Surgical treatment options are bothersome because correction and fusion of the deformation is incompatible with maintaining growth of the spine. Growing systems have also been used like growing rods, VEPTR, and recently magnetically controlled growing rods. However, these growing systems may require repeat operations or repeat elongations at certain intervals. These intervals are not similar to normal gradual growth of the spine, allow the spine to stiffen between lengthenings, lead to unphysiological strains on the tissues at the moment of lengthening, and can be a burden on the patient. In cases where surgical releases of the spine are to be performed, such as congenital deformations, the spine can re-fuse soon after operative release and static fixation with any current growth system and further growth may be impossible even with repetitive distractions.

SUMMARY OF THE INVENTION

In an aspect, there is disclosed a spinal distraction system comprising a bearing connector fastened to a fixated rod and a sliding rod, wherein the sliding rod includes a spring and a stop ring.

In another aspect, there is disclosed a method for distracting vertebrae, including inserting a first set of a plurality of fasteners into adjacent vertebrae in a first region; inserting a fixation rod into the first set of the plurality of fasteners; inserting a caudad end of the fixation rod into a bearing connector; inserting a second set of a plurality of fasteners into adjacent vertebrae in a second region; loading a stop ring and a spring onto the sliding rod; sliding the cephalad end of the sliding rod into the bearing connector so that the spring is disposed between the bearing connector and the stop ring; and inserting the caudad end of the sliding rod into the second set of a plurality of fasteners.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

Various embodiments of the present disclosure are described herein below with reference to the drawings, wherein.

DESCRIPTION OF ILLUSTRATIVE EMBODIMENTS

Figure 1A:
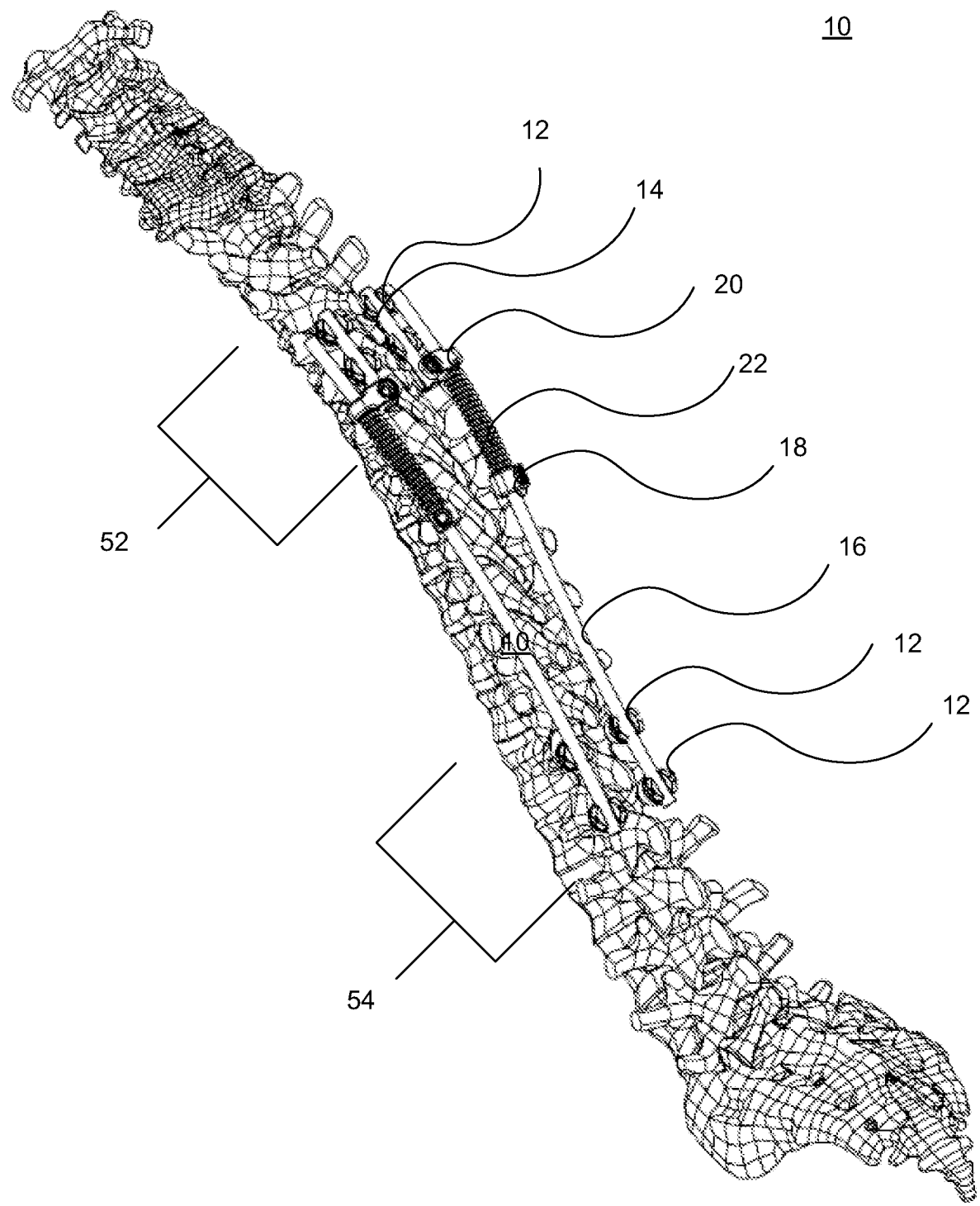
FIG. 1A is an isometric view of an example spinal distraction system according to an aspect of the present invention.

Various embodiments will now be described in detail with reference to the drawings, wherein like reference numerals identify similar or identical elements. In the drawings and in the description that follows, the term "proximal", as is traditional, will refer to the end of the device which is closest to the operator while the term "distal" will refer to the end of the device which is furthest from the operator. The term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e. away from the middle of the body of the patient). The term "posterior" indicates a direction toward the patient's back, and the term "anterior" indicates a direction toward the patient's front. Additionally, in the drawings and in the description that follows, terms such as front, rear, upper, lower, top, bottom and the similar directional terms are used simply for convenience of description and are not intended to limit the disclosure attached hereto.

Figure 1B:
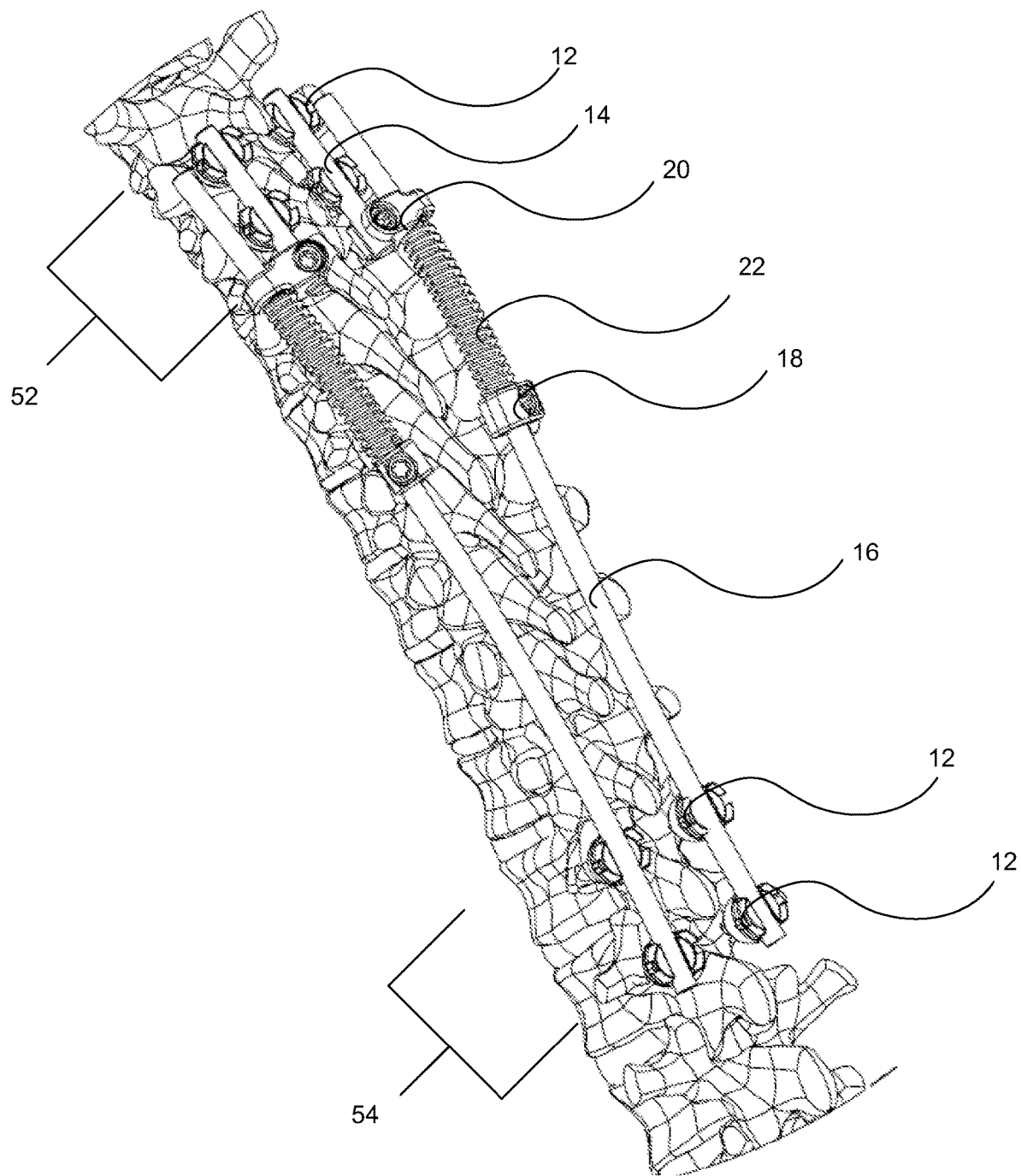
FIG. 1B is a close-up of FIG. 1A.

As shown in FIGS. 1A and 1B, the present disclosure is directed to a spinal distraction system 10 including a bearing connector 20 fastened to fixated rod 14 and a sliding rod 16, wherein the sliding rod 16 includes a spring 22 and a stop ring 18. The spinal distraction system 10 can provide continuous distraction to vertebrae. The magnitude of the distraction force can be adjusted intraoperatively by a surgeon based upon tactile feedback or a pre-tension/length table. Additionally, the spinal distraction system 10 can be used in combination with existing posterior spinal fusion systems.

FIGS. 2A-2E illustrate the bearing connector 20. The bearing connector 20 includes a set screw 24, a bearing 30, and a housing 21. The housing 21 can include a top surface 36, a bottom surface 38, and side surfaces 46, 47, as shown in FIGS. 3A-3B. The top surface 36 and the bottom surface 38 define a hollow 40 that can be configured and dimensioned to receive a rod, such as the fixated rod 14, as shown in FIGS. 1A-1B. The rod can be side-loaded into the hollow 40 and then secured in place by rotation of the set screw 24. Alternatively, the top surface 36 can have a defined hollow (not shown) that can be configured and dimensioned to receive the fixated rod 14. In this manner, the rod can be top-loaded into the hollow and then secured in place by rotation of a set screw that would be located on a side surface 46, 47. In an alternative embodiment, the bottom surface 38 can define a hollow that can be configured and dimensioned to receive the fixated rod 14. In this manner, the rod can be bottom-loaded into the hollow and then secured in place by rotation of a set screw that would be located on a side surface 46, 47.

Figure 2A:
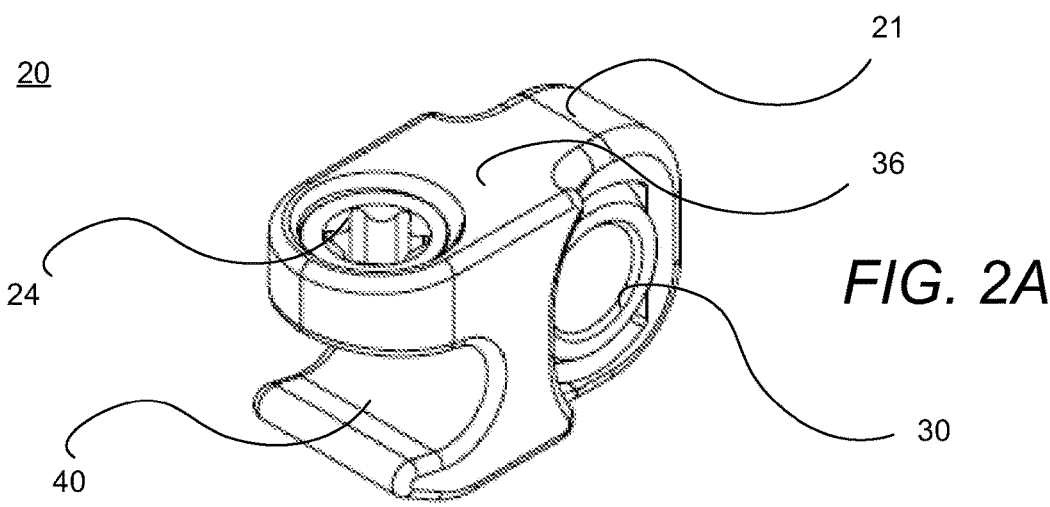
FIG. 2A is an example bearing connector according to an aspect of the present invention.
Figure 2B:
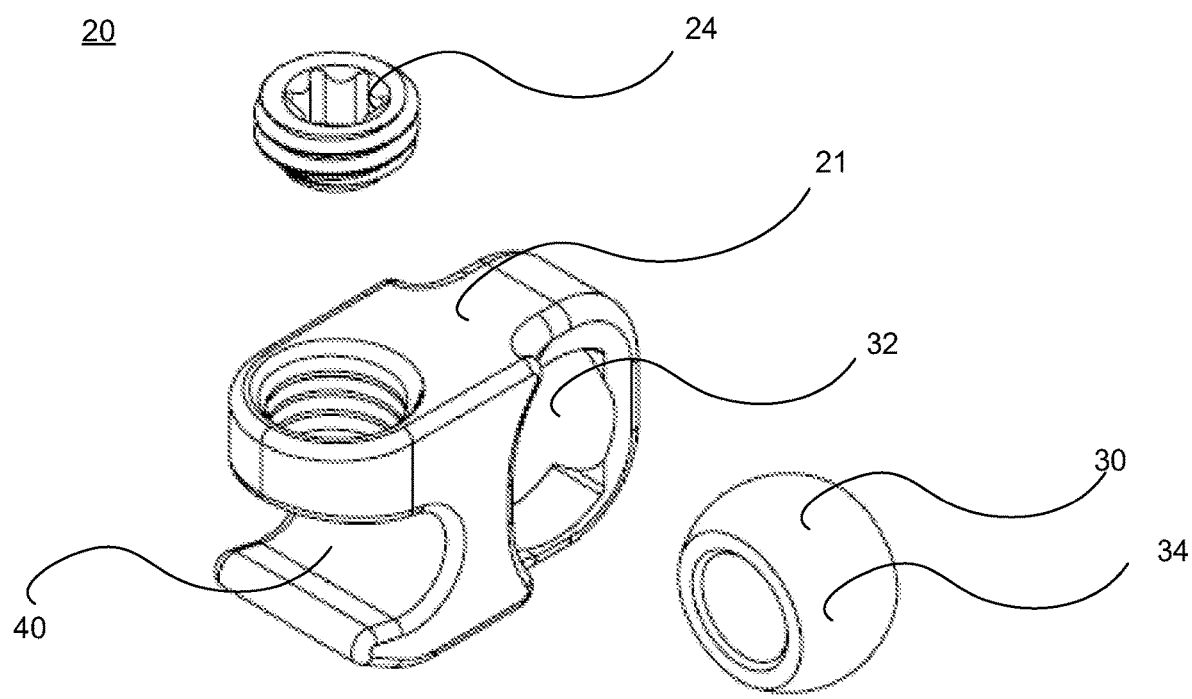
FIG. 2B is an exploded view of FIG. 2A.
Figure 2C:
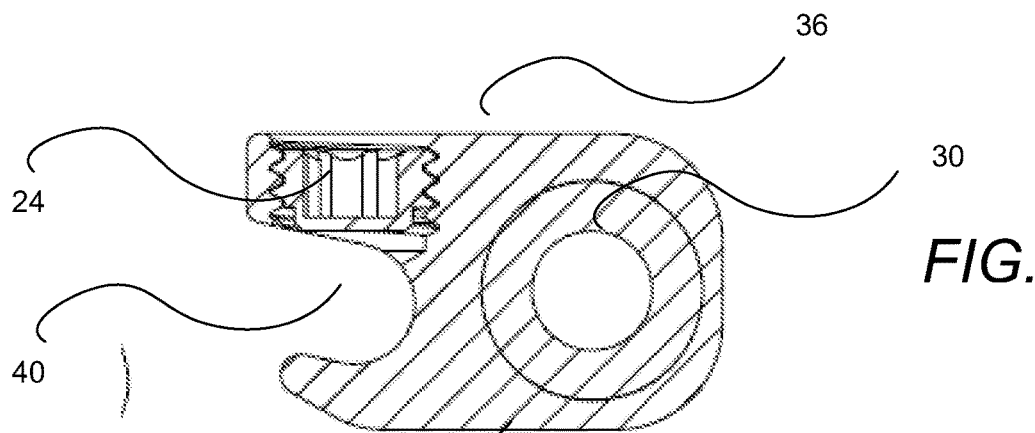
FIG. 2C is a cross-section of FIG. 2D.
Figure 2D:
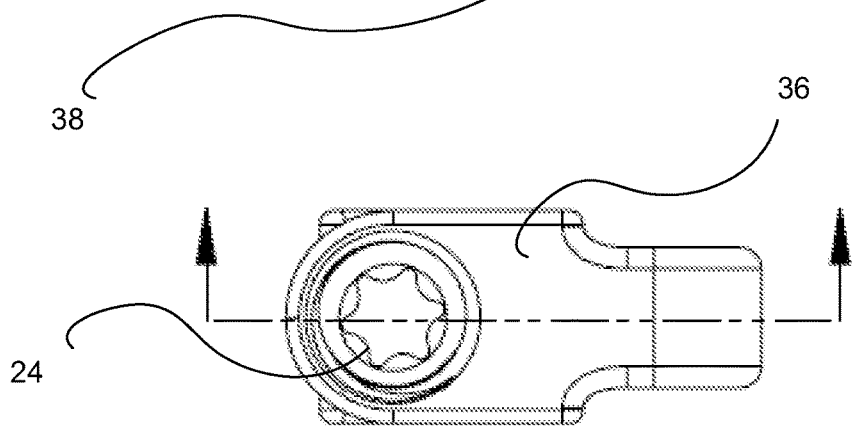
FIG. 2D is a top view of FIG. 2A.
Figure 2E:
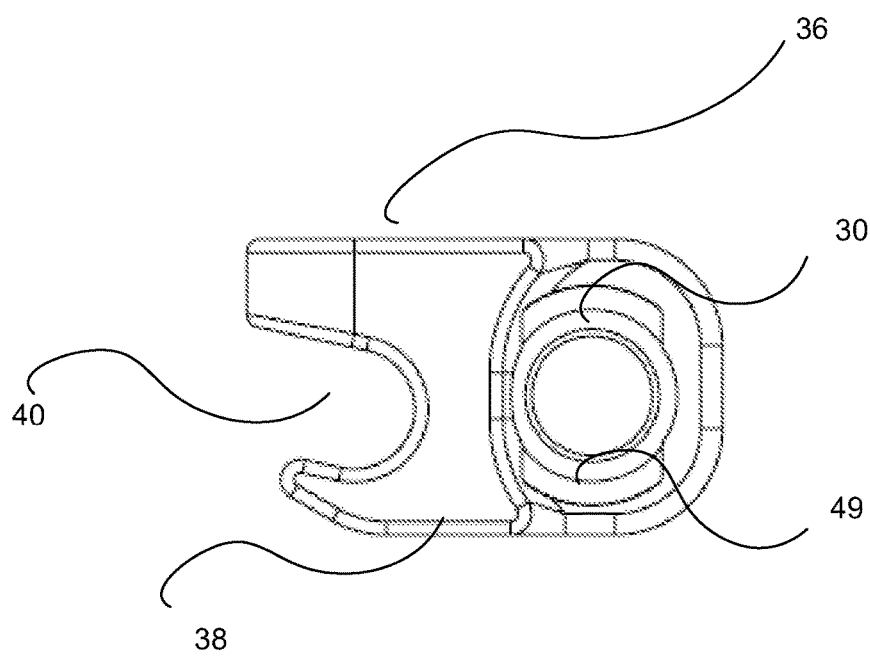
FIG. 2E is a side view of FIG. 2A.
Figure 3A:
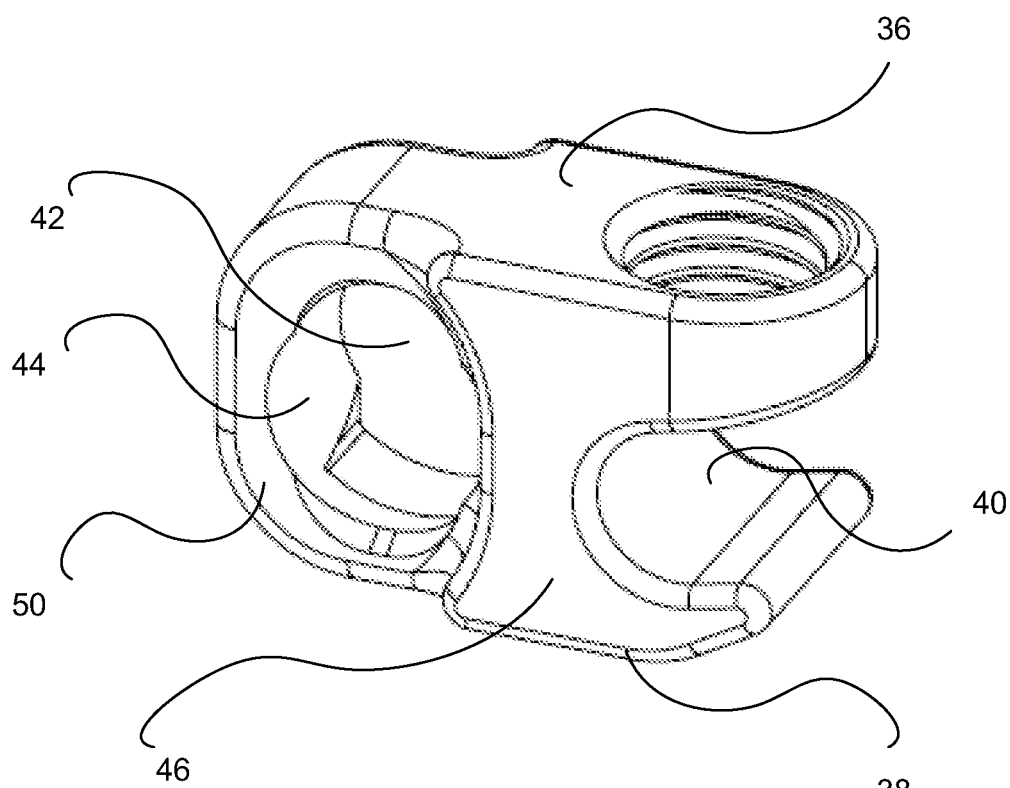
FIG. 3A is an isometric view of an example housing of the bearing connector according to an aspect of the invention.
Figure 3B:
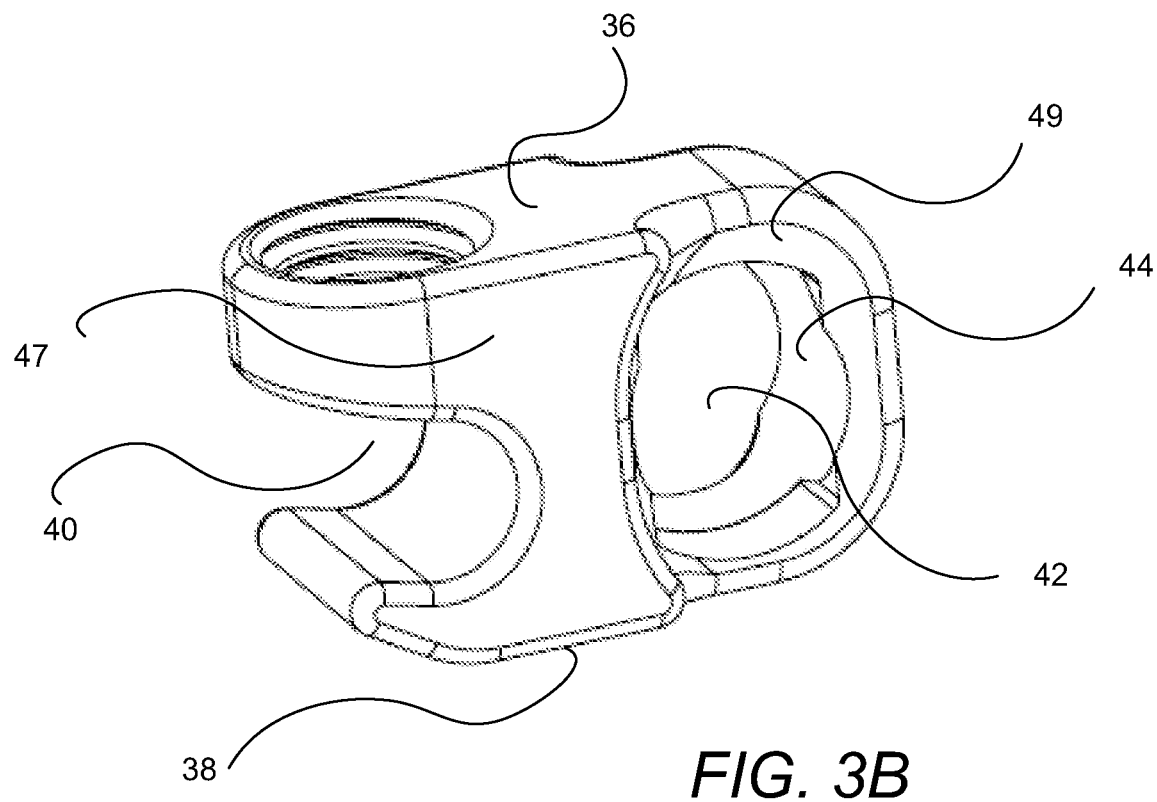
FIG. 3B is an alternative isometric view of FIG. 3A.
Figure 4A:
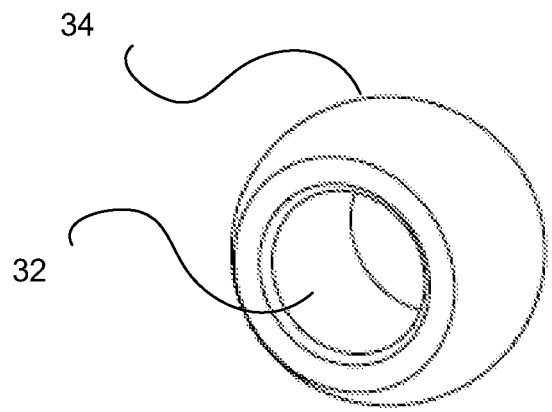
FIG. 4A is an isometric view of an example bearing of the bearing connector according to an aspect of the invention.
Figure 4B:
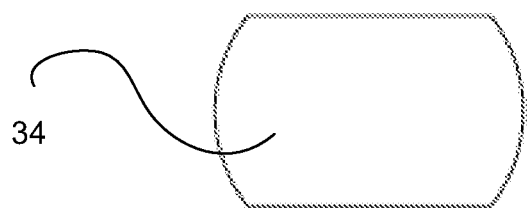
FIG. 4B is a top view of FIG. 4A.
Figure 4C:
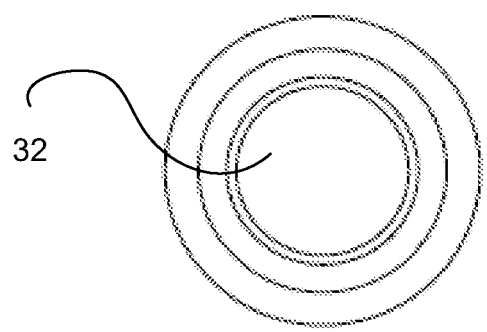
FIG. 4C is a side view of FIG. 4A.

As shown in FIGS. 2B, 3A, and 3B the housing 21 of the bearing connector 20 can include a first bore 42 that can extend from a first beveled side surface 49 to a second beveled side surface 50. In an aspect, the spring 22 can abut either of the first beveled side surface 49 or second beveled side surface 50. The first bore 42 can be configured and dimensioned to receive the bearing 30. In particular, the first bore 42 can include a concave inner surface 44 that mates with a convex outer surface 34 of the bearing 30. In this manner, the bearing 30 can freely rotate in a polyaxial manner within the housing 21 of the bearing connector 20. As shown in FIGS. 4A-4C, the bearing 30 can include a second bore 32 configured and dimensioned to receive the sliding rod 16.

The bearing connector 20 aligns passively with a rod, such as the sliding rod 16 with minimal friction. In this manner, there can be a reduction in growth resistance and metal debris. Metal debris can be associated with foreign body reactions, granuloma's and even low grade infections. The bearing connector 20 can also allow some sagittal motion, which can be enlarged by adding an extra rotational axis between the bearing connector 20 and the fastener 12. The ability of the spinal distraction system 10 to allow some sagittal motion also enables the spinal distraction system 10 to absorb energy which can prevent the spinal distraction system 10 from fatigue failure.

The spinal distraction system 10 can include, instead of the bearing connector 20, any connector that would provide for parallel connection of the fixated rod 14 and the sliding rod 16. For example, the connector could be two bores adjacent to one another with two set screws to secure the rods within, where one set screw is left out to allow sliding.

Figure 7:
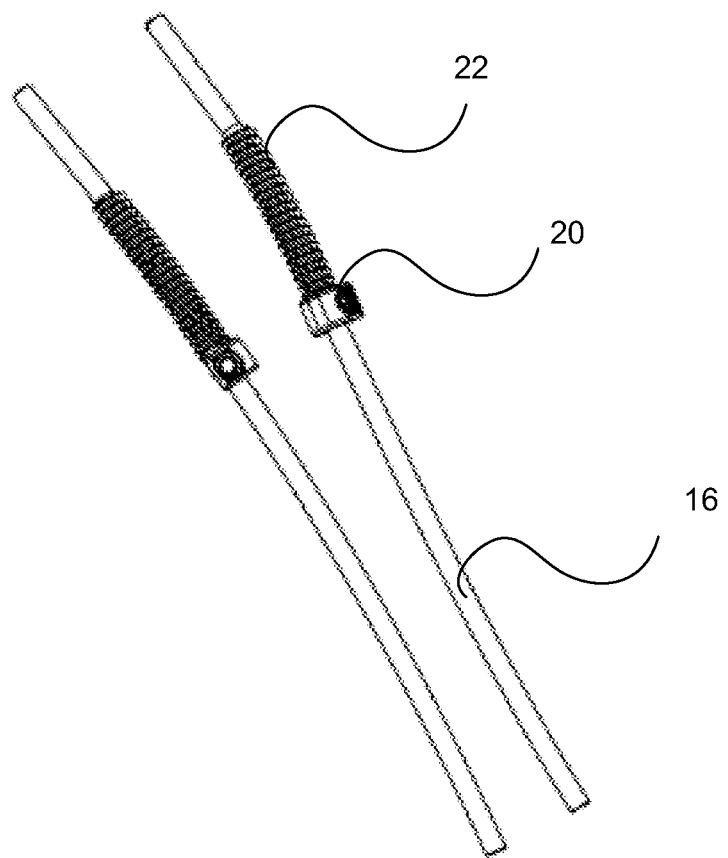
FIG. 7 is a view of an example sliding rod with a loaded spring and a stop ring according to an aspect of the invention.

As shown in FIG. 7, the sliding rod 16 can be loaded with a spring 22 and a stop ring 18. In an aspect, the spinal distraction system 10 can include a stop ring 18. The stop ring 18 can include a bore (not shown) and a set screw. The sliding rod 16 can be inserted through the bore of the stop ring 18. The stop ring 18 can be positioned anywhere along the length of the sliding rod 16. At a predetermined position, the set screw of the stop ring 18 can be tightened to secure the stop ring 18 along the sliding rod 16 at the predetermined position, such as after compression of the spring 22.

The spring 22 also contains a bore (not shown) that can be configured and dimensioned to receive a rod, such as the sliding rod 16. The spring 22 should be loaded so that one end of the spring 22 abuts the stop ring 18, as shown in FIG. 7. The spring 22 can be made of any biocompatible material including metals and polymers, such as titanium. The spring 22 can be any gauge so long as the spring 22 is able to distract the vertebrae over a period of time. In an aspect, the distraction force provided by the spring 22 should be about 50 to about 250 Newtons, for example from about 55 to about 225 Newtons, and as a further example from about 60 to about 200 Newtons. This distraction force can be provided by a spring 22 with a compressed length from about 3 to about 5 centimeters, such as about 3.2 to about 4.9 centimeters, and as a further example from about 4.3 to about 4.8 centimeters. The spring 22 can have an uncompressed (relaxed) length of about 3 to about 15 centimeters, for example from about 8 to about 13.8 centimeters, and as a further example from about 8.4 to about 9.6 centimeters. It should be noted that the spring 22 can be compressed during the initial installation of the spinal distraction system 10, but can also be compressed at any time thereafter depending upon the spinal growth. It is envisioned that any compression of the spring 22 after the initial compression would not be needed until several years later and would involve a minimal surgical procedure.

In an aspect, the spinal distraction system 10 can include one spring, two springs, three springs, etc. The number of springs 22 can be determined based upon the uncompressed length of the spring 22 as well as the optimal distracted length of the vertebrae. For example, the spinal distraction system 10 can include one spring 22 having an uncompressed length of 6 centimeters and a compressed length of 3 centimeters because the optimal distracted length of the involved vertebrae is 3 centimeters. Alternatively, the spinal distraction system 10 can include two springs 22 in series, each having an uncompressed length of 3 centimeters because the optimal distracted length of the involved vertebrae is 6 centimeters.

In an aspect, the spring 22 can be a mini-spring (not shown), for example, having an uncompressed length ranging from about 0.5 cm to about 3 cm, such as from about 0.75 cm to about 2.75 cm, including an uncompressed length from about 1.0 cm to about 2.5 cm. The mini-spring can be loaded onto a rod, such as the sliding rod 16 of the spinal distraction system 10. The mini-spring 22 can also be used with conventional growing rods and/or magnetically controlled rods, in combination with a sliding connector, leading to a more dynamic spinal fixation. Such a spinal distraction system including at least one mini-spring 22 can be less prone to fatigue failure and spontaneous fusion.

In an aspect, the spinal distraction system 10 can include a sleeve or sheath (not shown) that can extend over at least a portion of a length of the spring 22 to minimize tissue ingrowth. In an aspect, the sleeve extends over 50% of the length of the spring 22, for example over 75% of the length, and as a further example over 100% of the length of the spring 22. The sleeve or sheath could be a flexible tube, cloth, or woven material, for example. In another aspect, the spring 22 can be coated with a biocompatible material, such as a polymer, that prohibits and/or minimizes tissue growth. In another aspect, the spring 22 can be integrated in cellular foam with closed cells. The combination of the sleeve/sheath and spring 22 should not allow for any dead space which could provide an area susceptible to infection.

The spinal distraction system 10 can be used in multiples. For example, a spinal distraction system 10 can be used singly or can be used as a pair.

Figure 5:
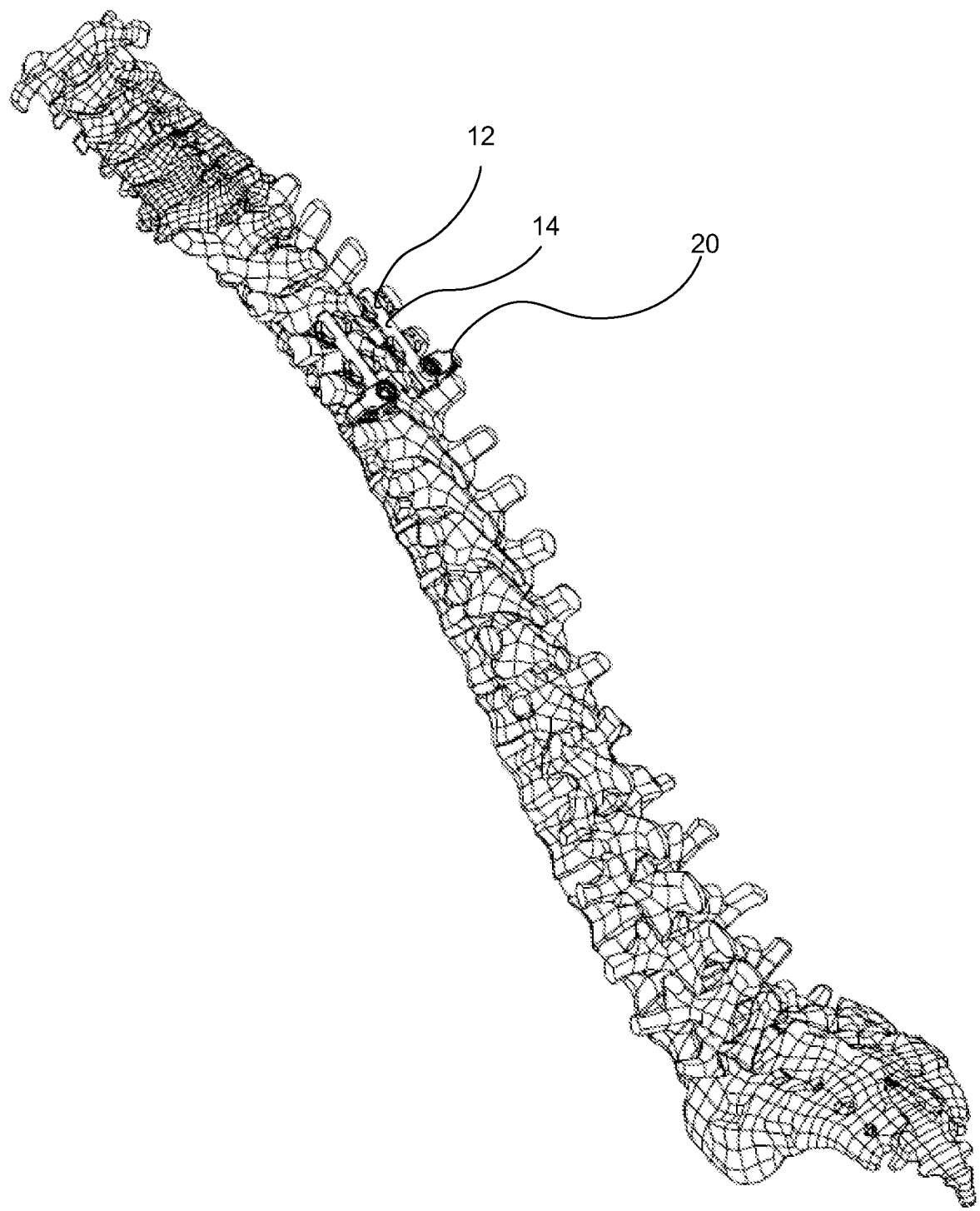
FIG. 5 is a view of an example fixated rod according to an aspect of the invention.

The spinal distraction system 10 can be used in a method for distracting vertebrae. The method includes forming a hole in a vertebra. In an aspect, two holes can be formed in a vertebra. In another aspect, two holes can also be formed into an adjacent vertebra. The vertebrae can each have two holes formed therein and can be in a first region 52, such as a cephalad region of a spinal column. Similarly, two holes can be formed in a vertebra and two holes can also be formed into an adjacent vertebra in a second region 54, such as a caudad region of a spinal column. The method can further include inserting into the formed holes a first set of a plurality of fasteners 12 into adjacent vertebrae in the first region 52, as shown in FIGS. 1A, 1B, and 5. One of ordinary skill in the art can determine the location along a length of the spinal column for the first region 52 relative to the second region 54.

The method can include inserting a first set of a plurality of fasteners 12 into the formed holes of adjacent vertebrae in the first region 52. An insertion tool can be used. The fasteners 12 can be any mechanical hardware, such as screws, including pedicle screws. In an aspect, each fastener of the plurality of fasteners 12 can include a head having a trough 56 configured and dimensioned to receive a rod, such as a fixated rod 14 and/or a sliding rod 16. In an aspect, the method can include inserting a fixated rod 14 into the first set of the plurality of fasteners 12. A caudad end of the fixated rod 14 can be inserted into a bearing connector 20, as shown in FIG. 5, such as the hollow 40 of the bearing connector 20. In another aspect, the bearing connector 20 can be inserted onto the caudad end of the fixated rod 14, and then the fixated rod 14 can be inserted into the troughs 56 of the first set of the plurality of fasteners 12. In an aspect, the method can further include locking the fixated rod 14 into the first plurality of fasteners 12.

Figure 6:
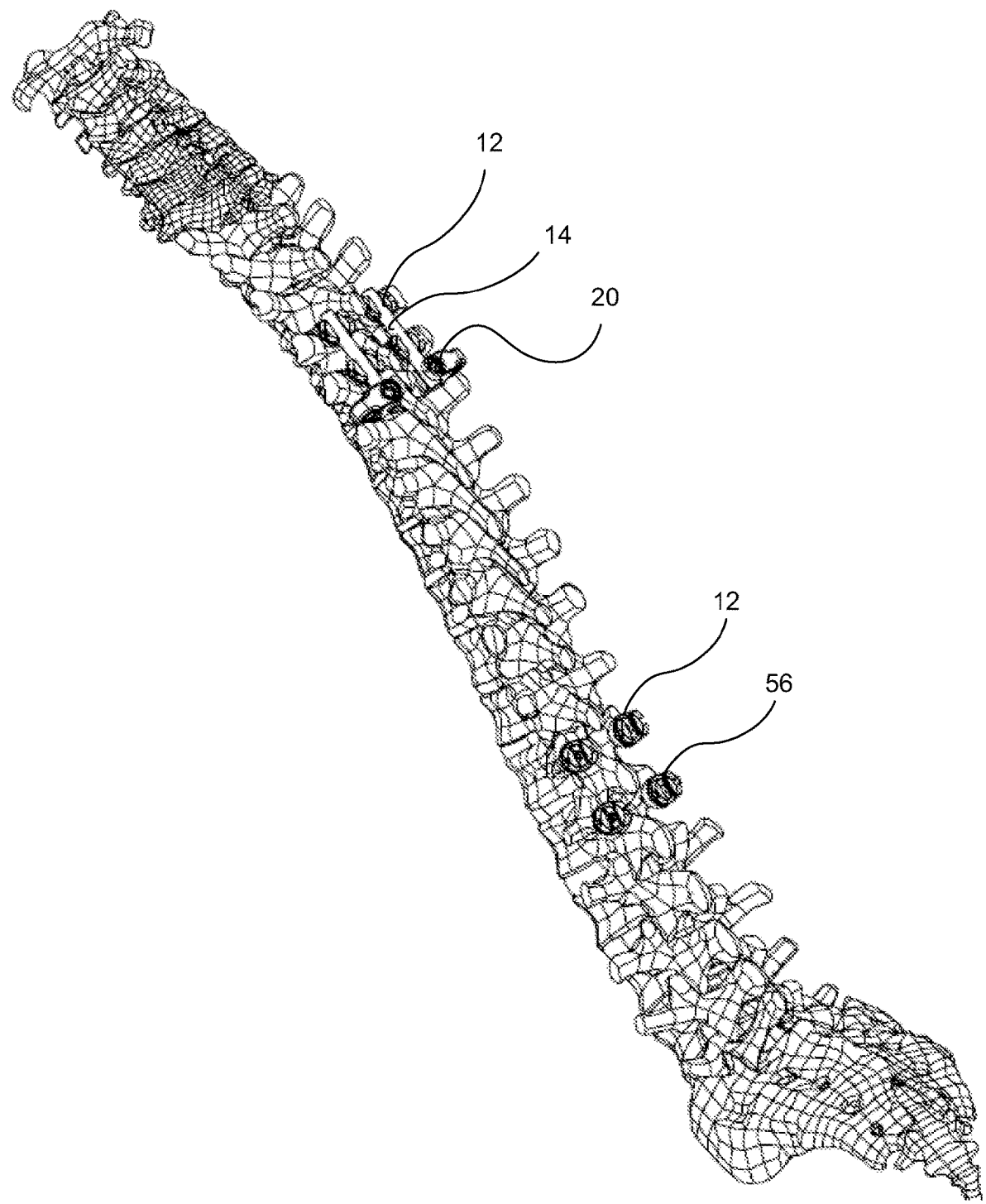
FIG. 6 is a view of an example fixated rod and fasteners according to an aspect of the invention.

The method can include inserting a second set of a plurality of fasteners 12 into adjacent vertebrae in a second region 54, as shown in FIG. 6. One of ordinary skill in the art will realize that this step can also be performed at the same time as inserting the first set of a plurality of fasteners 12 into adjacent vertebrae in the first region 52. In particular, the first and second set of the plurality of fasteners 12 can be inserted into the insertion holes in any order, i.e., first region 52 and then second region 54, or second region 54 and then first region 52. Additionally, both of the first and second set of the plurality of fasteners 12 can be inserted before the fixated rod 14 is inserted into the first region 52. In an aspect, the method can further include locking the sliding rod 16 into the second set of plurality of fasteners 12.

The method can include loading a stop ring 18 and a spring 22 onto a sliding rod 16, as shown in FIG. 7. Once the stop ring 18 is positioned at a predetermined location along a length of the sliding rod 16 a set screw associated with the stop ring 18 can be rotated to tighten the stop ring 18. In an aspect, the set screw associated with the stop ring 18 can be left loose until a later time, such as after the spring 22 are compressed. In an aspect, the sliding rod 16 can be bent along its length before loading of the spring 22 and the stop ring 18.

Figure 8:
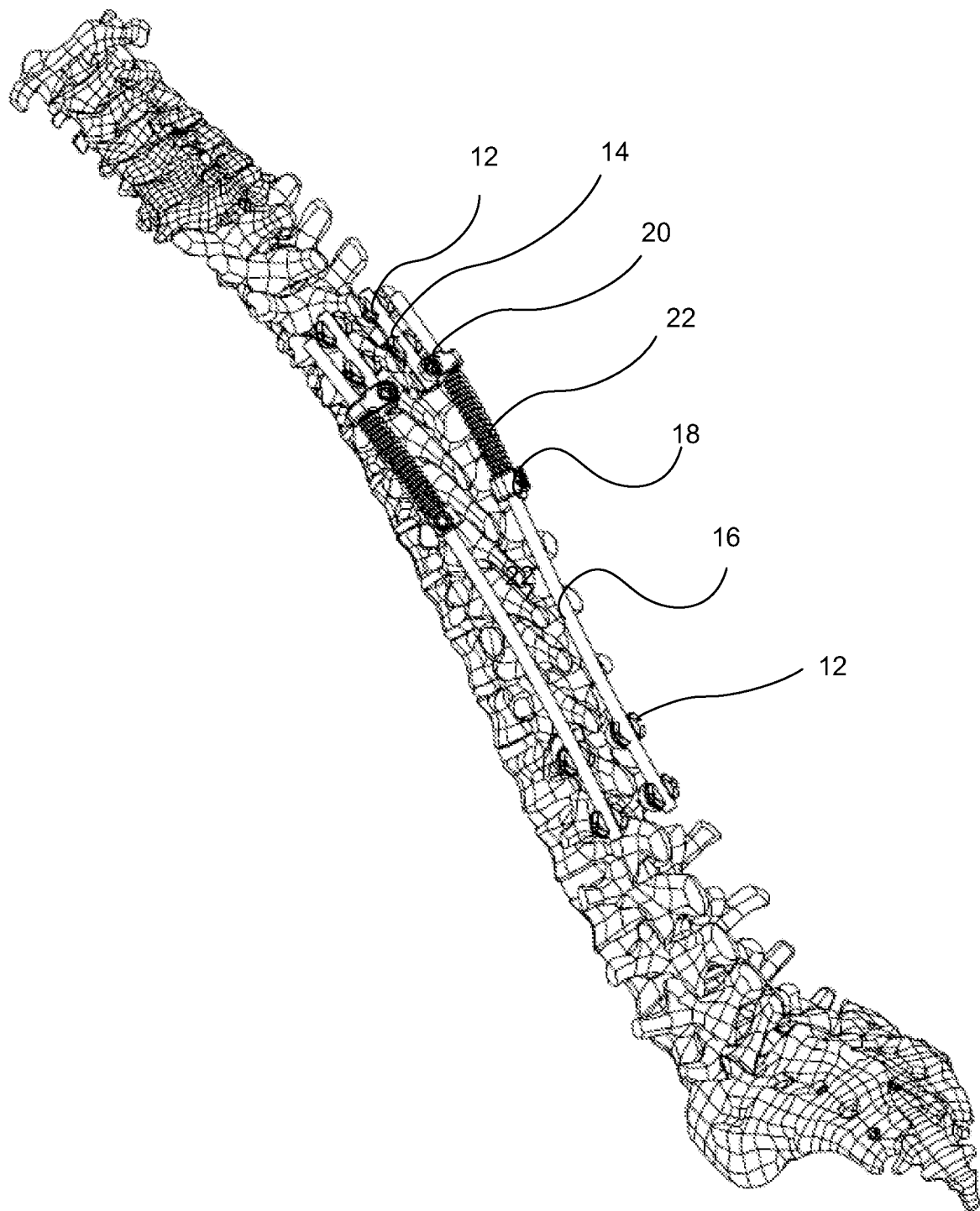
FIG. 8 is a view of the sliding rod inserted into the bearing connector according to an aspect of the invention.

The method can include sliding an end of the sliding rod 16 into the bearing connector 20 so that the spring 22 is disposed between the bearing connector 20 and the stop ring 18, as shown in FIG. 8. In particular, a cephalad end of the sliding rod 16 can be inserted into a bearing of the bearing connector 20. A portion of the sliding rod 16 can extend through and beyond the bearing connector 20. The spring 22 can abut a beveled side surface 49 of the bearing connector 20 at one end and the stop ring 18 on another end. In an aspect, the portion of the sliding rod 16 that extends beyond the bearing connector 20 can be parallel to the fixated rod 14. An opposite end of the sliding rod 16 can extend towards and beyond the second set of the plurality of fasteners 12 in the second region 54. The opposite end of the sliding rod 16 can be inserted into the second set of a plurality of fasteners 12. The bearing connector 20 can provide continuous alignment with the sliding rod 16 and sagittal motion.

Figure 9:
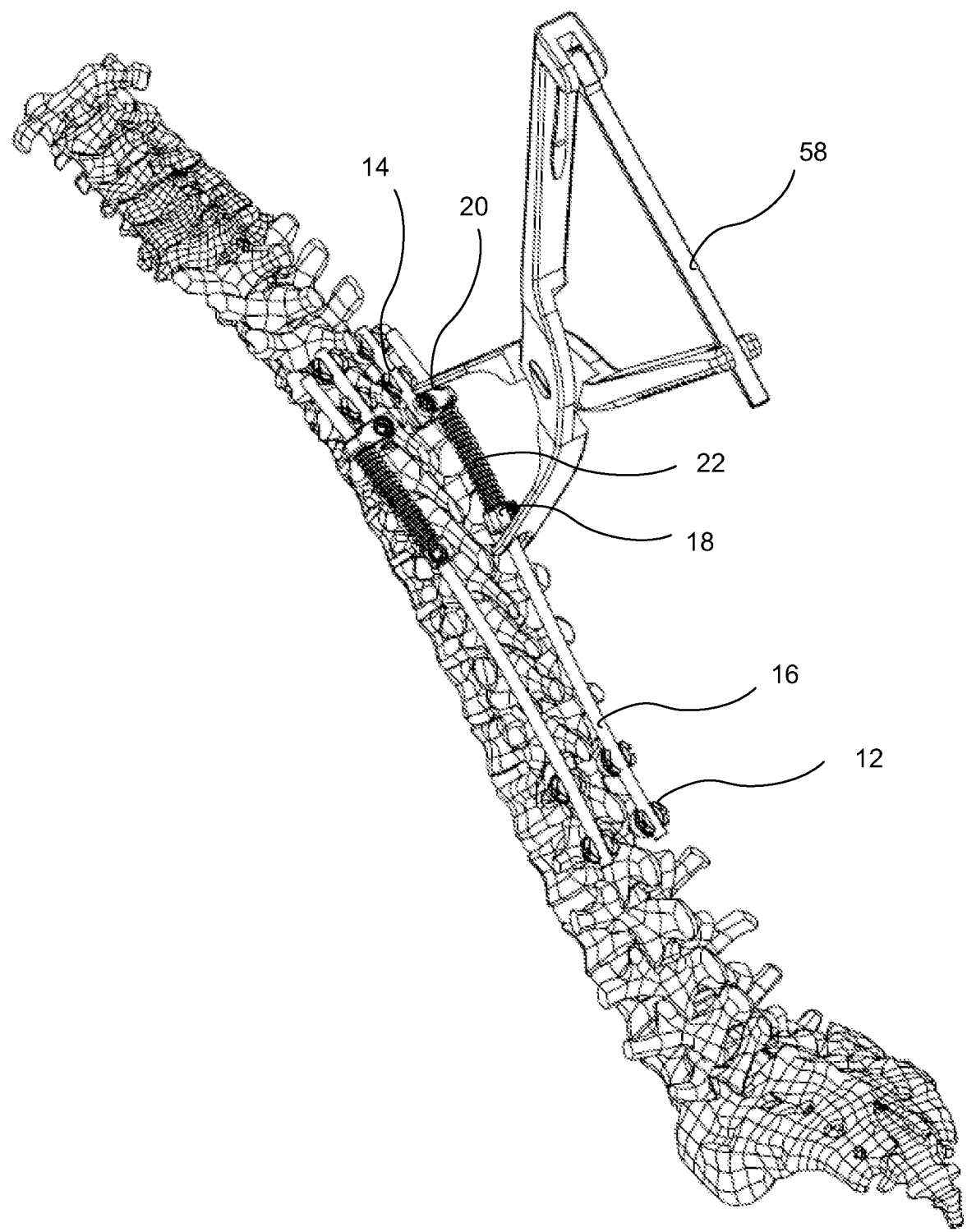
FIG. 9 is a view of a compressor compressing the spring and stop ring according to an aspect of the invention.

The method can further include compressing the spring 22, as shown in FIG. 9. An instrument 58 can be positioned so that the bearing connector 20, spring 22, and stop ring 18 are between the ends of the instrument 58. A force can be applied to a handle of the instrument 58 so that the stop ring 18 applies a force against the spring 22 thereby compressing the spring 22 against the bearing connector 20. A force can be applied to the set screw associated with the stop ring 18 locking the stop ring 18 in place against the compressed spring 22.

The method can further include compressing the spring 22 a second time after a period of time to provide a continuous distraction of the vertebrae.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for distracting vertebrae, comprising:
   inserting a first set of a plurality of fasteners into adjacent vertebrae in a first region;
   inserting a fixated rod into the first set of the plurality of fasteners;
   inserting a caudad end of the fixated rod into a single bearing connector;
   inserting a second set of a plurality of fasteners into adjacent vertebrae in a second region;
   loading a stop ring and a spring onto a sliding rod;
   sliding an end of the sliding rod into the single bearing connector so that the spring is disposed between the single bearing connector and the stop ring;
   inserting an opposite end of the sliding rod into the second set of the plurality of fasteners and
   sliding the stop ring along a length of the sliding rod to a location spaced from the second set of the plurality of fasteners to compress the spring.

2. The method of claim 1, wherein the bearing connector includes a set screw, a bearing and a housing, wherein the housing has a top surface and a bottom surface that define a hollow.

3. The method of claim 2, wherein the hollow is configured and dimensioned to receive the fixated rod.

4. The method of claim 1, wherein the bearing connector includes a first bore that extends from a first beveled side surface to a second beveled side surface.

5. The method of claim 4, wherein the first bore is configured and dimensioned to receive a bearing.

6. The method of claim 5, wherein the bearing includes a second bore configured and dimensioned to receive the sliding rod.

7. The method of claim 4, wherein the first bore includes a concave inner surface.

8. The method of claim 1, wherein the spring abuts a beveled side surface of the bearing connector.

9. The method of claim 1, further comprising extending a sleeve over at least a portion of a length of the spring.

10. The method of claim 1, further comprising locking the fixation rod into the first plurality of fasteners.

11. The method of claim 1, further comprising locking the sliding rod into the second set of plurality of fasteners.

12. The method of claim 1, further comprising locking the stop ring.

13. The method of claim 1, further comprising bending the sliding rod before the stop ring and the spring are loaded.

14. The method of claim 1, wherein the caudad end of the fixation rod is inserted into a hollow of the bearing connector.

15. The method of claim 1, wherein the cephalad end of the sliding rod is inserted into a bearing of the bearing connector.

16. The method of claim 1, further comprising compressing the spring a second time after a period of time to provide continuous distraction of the vertebrae.

17. The method of claim 1, wherein the bearing connector provides continuous alignment with the sliding rod and sagittal motion.

* * * * *